(12) United States Patent
Fleming

(10) Patent No.: US 8,815,607 B2
(45) Date of Patent: *Aug. 26, 2014

(54) SELF-CONTAINED TEST SENSOR

(71) Applicant: Bayer HealthCare LLC, Whippany, NJ (US)

(72) Inventor: Roger Fleming, Niles, MI (US)

(73) Assignee: Bayer Healthcare LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/096,849

(22) Filed: Dec. 4, 2013

(65) Prior Publication Data
US 2014/0093895 A1 Apr. 3, 2014

Related U.S. Application Data

(63) Continuation of application No. 11/792,360, filed as application No. PCT/US2005/044810 on Dec. 12, 2005, now Pat. No. 8,691,161.

(60) Provisional application No. 60/635,721, filed on Dec. 13, 2004.

(51) Int. Cl.
G01N 21/75 (2006.01)
G01N 35/00 (2006.01)
B01L 3/00 (2006.01)

(52) U.S. Cl.
CPC ............... *G01N 35/00* (2013.01); *B01L 3/502* (2013.01); *B01L 3/502707* (2013.01)
USPC ........... 436/165; 422/412; 422/401; 422/420; 422/68.1; 422/525

(58) Field of Classification Search
CPC .... G01N 35/00; B01L 3/502; B01L 3/502707
USPC .......... 422/401, 412, 420, 68.1, 525; 436/165
See application file for complete search history.

(56) References Cited

U.S. PATENT DOCUMENTS 3,697,227 A 10/1972 Goldstein et al.
3,799,742 A 3/1974 Coleman et al.
(Continued)

FOREIGN PATENT DOCUMENTS

EP 1 022 562 7/2000
EP 1 022 565 7/2000
(Continued)

OTHER PUBLICATIONS

European Search Report for EP Application No. EP 10 16 4464, dated Sep. 7, 2010, 2 pages.
(Continued)

*Primary Examiner* — Lyle Alexander
(74) *Attorney, Agent, or Firm* — Nixon Peabody LLP

(57) ABSTRACT

A test strip to assist in determining the concentration of an analyte in a fluid sample comprises a base, at least one tab and a break line. The base includes a capillary channel and a test element. The capillary channel is in fluid communication with the test element. The test element is adapted to receive the fluid sample. The at least one tab is removably attached to the base. The capillary channel extends from the base into a portion of the tab. The break line intersects the capillary channel in which an inlet to the capillary channel is exposed along the break line when the tab is separated from the base.

22 Claims, 10 Drawing Sheets

(56) References Cited

U.S. PATENT DOCUMENTS

| | | | |
|---|---|---|---|
| 5,234,813 | A | 8/1993 | McGeehan et al. |
| 5,863,800 | A | 1/1999 | Eikmeier et al. |
| 5,888,832 | A | 3/1999 | Richardson |
| 5,962,333 | A | 10/1999 | Incorvia et al. |
| 6,071,294 | A | 6/2000 | Simons et al. |
| 6,090,124 | A | 7/2000 | Weekes et al. |
| 6,090,347 | A * | 7/2000 | Emodi ................ 422/401 |
| 6,180,063 | B1 | 1/2001 | Markart |
| 6,682,704 | B2 | 1/2004 | Bottwein et al. |
| 6,740,293 | B1 * | 5/2004 | Deng ................ 422/412 |
| 7,473,400 | B2 | 1/2009 | Wantanabe et al. |
| 2001/0027277 | A1 | 10/2001 | Klitmose |
| 2003/0047451 | A1 * | 3/2003 | Bhullar et al. ....... 204/403.01 |
| 2003/0175155 | A1 * | 9/2003 | Charlton ................ 422/61 |
| 2003/0211619 | A1 | 11/2003 | Olson et al. |
| 2004/0184964 | A1 * | 9/2004 | Watanabe et al. ....... 422/100 |

FOREIGN PATENT DOCUMENTS

| | | |
|---|---|---|
| EP | 1 174 716 | 1/2002 |
| EP | 1 360 932 A | 11/2003 |
| JP | 2002-036196 | 2/2002 |
| JP | 2002-066399 | 3/2002 |
| JP | 2002-066999 | 3/2002 |
| JP | 2002-282682 | 10/2002 |
| JP | 2004-286501 A | 10/2004 |
| WO | WO 02/50609 | 6/2002 |
| WO | WO03/082092 | 10/2003 |
| WO | WO03/083469 | 10/2003 |
| WO | WO2004/105946 | 12/2004 |

OTHER PUBLICATIONS

European Search Report for EP Application No. EP 10 16 4463, dated Sep. 9, 2010, 2 pages.

International Search Report corresponding to co-pending International Patent Application No. PCT/US2005/044810, European Patent Office, dated Aug. 21, 2006, 6 pages.

Written Opinion of the International Searching Authority corresponding to co-pending International Patent Application No. PCT/US2005/044810, European Patent Office, dated Aug. 21, 2006, 7 pages.

* cited by examiner

SELF-CONTAINED TEST SENSOR

This application is a continuation of U.S. application Ser. No. 11/792,360, filed Jun. 5, 2007, now U.S. Pat. No. 8,691,161, which was the National Stage of International Application No. PCT/US2005/044810, filed Dec. 12, 2005, which claims the benefit of U.S. Provisional Application No. 60/635,721 filed Dec. 13, 2004, each of which is hereby incorporated by reference herein in its entirety.

FIELD OF THE INVENTION

The present invention relates generally to diagnostic instruments and, more particularly, to individually desiccated diagnostic test strips and a method for using the same.

BACKGROUND OF THE INVENTION

Test strips (e.g., biosensors) containing reagents are often used in assays for determining the analyte concentration in a fluid sample. The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. Each test requires that a new test sensor be used, and thus, a number of test strips may be used in a single day. Cartridges that contain a number of test strips are used to allow users to carry multiple strips around within a single object. These cartridges may also be incorporated directly into a meter.

One of the difficulties in designing a meter or cartridge containing multiple test stripes in a compact housing (stacked like sticks of chewing gum in a package) is how to provide the desiccation required to prevent or inhibit strip deterioration. If the cartridge or meter itself is the primary container, the adequate resealing of the package once the first test strip is removed is a problem. If each test strip is individually foiled, the foil (a) may get in the way of strip handling and/or (b) make it more difficult to automatically move or discard the strip with a device.

One approach to individual test strip desiccation is to individually package the test strips as a continuous reel. This approach generates a lot of trash from the packaging that is fed back into the strip cartridge. This trash provides an increased likelihood of misfeeding the packaging scrap, thus, resulting in jams. This approach also mandates a larger package to accommodate the trash. Alternatively, another approach is to create separated individual compartments within the cartridge or meter. However, this approach does not provide for efficient stacking of test strips in a compact housing. Another approach is to foil the test strips with an individual desiccant. Typically, in this approach, the desiccant is outside of the test strip itself. Additionally, a lot of excess packaging (the foil) is required whose removal is difficult to integrate with an automatic strip feed system.

Therefore, it would be desirable to have a system and method for desiccating a diagnostic test strip that addresses these issues.

SUMMARY OF THE INVENTION

A test strip to assist in determining the concentration of an analyte in a fluid sample is disclose, according to one embodiment of the present invention. The test strip includes a base including a capillary channel and a test element. The capillary channel is in fluid communication with the test element and the test element is adapted to receive the fluid sample. The test strip includes at least one tab removably attached to the base. The capillary channel extends from the base into a portion of the tab. The test strip further includes a break line intersecting the capillary channel. An inlet to the capillary channel is exposed along the break line when the tab is separated from the base.

According to another embodiment of the present invention, a method for using a test strip to determine a concentration of an analyte in a fluid sample is disclosed. The method includes the act of providing a test strip including (i) a base including a capillary channel and a test element, (ii) at least one tab removably attached to the base, and (iii) a break line intersecting the capillary channel. The capillary channel is in fluid communication with the test element that is adapted to receive the fluid sample. The capillary channel extends from the base into a portion of the tab. The method further includes the act of exposing an inlet to the capillary channel by at least partially separating the at least one tab from the base.

According to yet another embodiment of the present invention, a test strip to assist in determining the concentration of an analyte in a fluid sample is disclosed. The test strip includes a base including a capillary channel and a test element. The capillary channel is in fluid communication with the test element that is adapted to receive the fluid sample. The test strip further includes a tab removably attached to the base. The capillary channel extends from the base into a portion of the tab. The test strip further includes a protrusion extending from the base into the tab. The protrusion is an extension of the capillary channel into the tab. The test strip further includes a break line intersecting the capillary channel. An inlet to the capillary channel is exposed when the tab is separated from the base. The inlet is located at the end of the protrusion opposite the base.

According to one embodiment of the present invention, a test strip to assist in determining the concentration of an analyte in a fluid sample is disclosed. The test strip includes a base and at least one tab. The base includes an upper surface, a capillary channel, a test element, and a desiccant. The capillary channel is in fluid communication with the test element that is adapted to receive the fluid sample. The at least one tab is removably attached to the upper surface of the base. The at least one tab includes a lip that extends from the base. The lip is adapted to allow the at least one tab to be separated such that the separation from the base exposes an inlet to the capillary channel.

According to another embodiment of the present invention, a test strip to assist in determining the concentration of an analyte in a fluid sample is disclosed. The test strip includes a base including a capillary channel, a test element, and a vent channel. The test element is adapted to receive the fluid sample. The capillary channel, test element, and vent channel are in communication with one another. The test strip includes a first and second tab removably attached to the base opposite each other. The capillary channel extends from the base into a portion of the first tab and the vent channel extends from the base into a portion of the second tab. The test strip includes a first break line intersecting the capillary channel and a second break line intersecting the vent channel. An inlet to the capillary channel is exposed when the first tab is separated from the base, whereas a vent to the vent channel is exposed when the second tab is separated from the base.

According to yet another embodiment of the present invention, a test strip to assist in determining the concentration of an analyte in a fluid sample is disclosed. The test strip includes a base including a capillary channel and a test element. The capillary channel is in fluid communication with the test element. The test element is adapted to receive the fluid sample. The test strip also includes a tab having a body and at least one extension extending from the body of the tab. The at least one extension removably attaches the base to the tab. The at least one extension is adapted to separate from the base when the tab is rotated relative to the base.

According to one embodiment of the present invention, a test strip to assist in determining the concentration of an analyte in a fluid sample is disclosed. The test strip includes a base including a capillary channel and a test element. The capillary channel is in fluid communication with the test element. The test element is adapted to receive the fluid sample. The test strip further includes at least one tab removably attached to the base. The at least one tab is located perpendicular to the base. The at least one tab being adapted to bend toward the base to expose an inlet to the capillary channel.

According to another embodiment of the present invention, a meter adapted to incorporate a test strip to assist in determining the concentration of an analyte in a fluid sample. The meter includes a face having a read-head located therein and a plurality of projections extending from the face. The plurality of projections are adapted to seat the test strip thereon. The test strip includes (i) a base including a capillary channel and a test element, (ii) at least one tab removably attached to the base, and (iii) a break line intersecting the capillary channel. The capillary channel is in fluid communication with the test element that is adapted to receive the fluid sample. The capillary channel extends from the base into a portion of the tab. An inlet to the capillary channel is exposed along the break line when the tab is separated from the base.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 10b is an upper perspective view of a meter adapted to seat the test strip of FIG. 10a.

DESCRIPTION OF ILLUSTRATED EMBODIMENTS

The present invention is directed to the protection of individual, dry-phase test strips from moisture. The test strips are adapted to be used in conjunction with a meter that can analyze (and in some embodiments, dispense) the test strips. The present invention may be utilized in dry-phase diagnostic test devices and can be applied to home-use kits, doctors' office kits, and hospital instruments using dry-phase tests.

The meter and test strip may be used to determine concentrations of at least one analyte in a fluid sample on the test strip. Analytes that may be measured using the present invention include glucose, lipid profiles (e.g., cholesterol, triglycerides, LDL and HDL), microalbumin, hemoglobin $A_1C$, fructose, lactate, bilirubin, or prothrombin. The present invention is not limited, however, to these specific analytes and it is contemplated that other analyte concentrations may be determined. The analytes may be in, for example, a whole blood sample, a blood serum sample, a blood plasma sample, other body fluids like ISF (interstitial fluid) and urine, or other (non-body) fluid samples. As used within this application, the term "concentration" refers to an analyte concentration, activity (e.g., enzymes and electrolytes), titers (e.g., antibodies), or any other measure concentration used to measure the desired analyte.

Figure 1A:
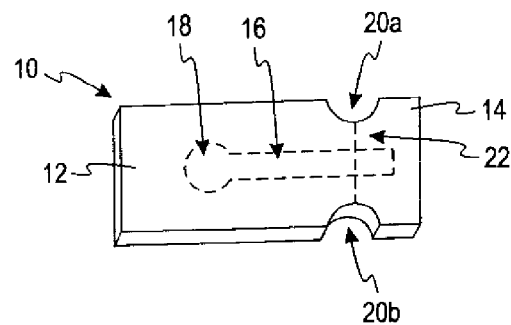
FIG. 1a is an upper perspective view of a test strip, according to one embodiment of the present invention.
Figure 1B:
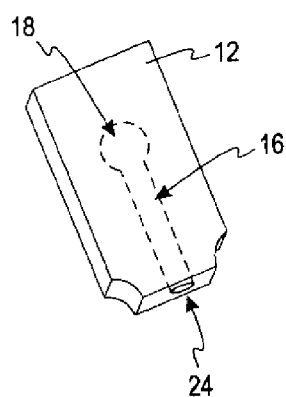
FIG. 1b is an upper perspective view of the test strip of FIG. 1a after the tab has been separated from the base.

Turning now to the drawings and initially to FIGS. 1a-b, a test strip 10 is illustrated according to one embodiment of the present invention. The test strip 10 comprising a base 12 with a tab 14 removably attached to the base 12. A capillary channel 16 is provided that is in fluid communication with a test element 18. The capillary channel 16 is adapted to transport a fluid sample from a sample site to the test element 18.

The terms removably attached or attached, as used herein, refer to any attachment of two sections through any suitable means, wherein the two sections may be separated via force. Further, the terms removably attached or attached, as used herein, refer to one continuous piece of material, wherein two portions of the continuous piece of material may be separated from one another via force.

The test strip 10 also includes recesses 20a,b located between the base 12 and the tab 14. The recesses 20a,b are provided to facilitate the separation of the tab 14 from the base 12 of the test strip 10 along a break line 22. The break line 22 may be created by the recesses 20a,b alone, or the break line 22 may be scored, a cut-line, a line of weakness, a thinned area/line, etc. The break line 22 intersects a portion of the capillary channel 16. When the tab 14 is separated from the base 12 along the break line 22, an inlet 24 is exposed. The inlet 24 allows a fluid sample to enter the capillary channel 16 where it is transported to the test element 18. In some embodiments, the intersection of the break line 22 with the capillary channel 16 is within the channel itself. In other embodiments, the break line 22 intersects above, below, and/or along side the channel and need not physically touch or be part of the channel.

The test element 18 may contain at least one reactant adapted to react with one or more analyte of interest in the fluid sample. The reaction between the at least one reactant and the fluid sample may then be monitored by a meter to determine the concentration of the analyte. The reaction may designed to be monitored optically or electrochemically.

In some embodiments of the present invention, for example, the test element 18 could contain reagents adapted for the optical determination of glucose, such as the enzyme glucose oxidase in combination with indicators such as tetramethylbenzidine or dianisidine or 4-aminoantipyrine plus p-hydroxybenzenesulfonate in the presence of peroxidase. In other embodiments, the enzyme glucose dehydrogenase could be used in combination with tetrazolium indicators such as p-iodonitrotetrazolium violet (INT), nitroblue tetrazolium (NBT) or tetranitroblue tetrazolium (TNBT), for example.

In yet other embodiments of the present invention where the analyte is cholesterol, the test element 18 may contain the enzymes cholesterol ester hydrolase and cholesterol oxidase plus indicators such as tetramethylbenzidine or dianisidine or 4-aminoantipyrine plus p-hydroxybenzenesulfonate in the presence of peroxidase.

In other embodiments, where the analytes are triglycerides, the enzymes lipase, glycerokinase, glycerolphosphate dehydrogenase and diaphorase in combination with tetrazolium indicators such as p-iodonitrotetrazolium violet (INT), nitroblue tetrazolium (NBT) or tetranitroblue tetrazolium (TNBT) will produce a color indicative of the triglyceride levels. In yet other embodiments, the enzymes lipase, glycerokinase, glycerol phosphate oxidase combined with indicators such as tetramethylbenzidine or dianisidine or 4-aminoantipyrine plus p-hydroxybenzenesulfonate in the presence of peroxidase will produce color in response to triglycerides.

According to other embodiments of the present invention, where the analyte is the enzyme amylase, the test element may contain, for example, the enzyme alpha glucosidase and the chromogenic indicator 4,6-ethylidene (G7) nitrophenyl (G1)-(alpha)D-maltoheptoside. In still other embodiments, hemoglobin can be detected using, for example, potassium ferricyanide, potassium cyanide and sodium bicarbonate.

In some embodiments, the test element 18 may contain reagents adapted for the electrochemical determination of an analyte concentration. In these embodiments, the test element includes at least one appropriately selected enzyme to react with the desired analyte or analytes to be tested. An enzyme that may be used to electrochemically react with glucose, for example, is glucose oxidase. It is contemplated that other enzymes may be used such as glucose dehydrogenase. In other embodiments of the present invention, the test strip 10 may be adapted to allow the determination of the concentration of an analyte in a fluid sample viscosimetrically or thermally.

Upon applying the sample to the test element 18, the analyte reacts with the at least one reagent located on the test element 18. The reaction is indicative of the analyte concentration in the sample and is evaluated using an optical readhead located in a meter. As discussed above, the test strips of the present invention may be used in combination with meters having other detection schemes. In other schemes, such as, electrochemical, etc. different reactants may be applied to the test element 18 to generate the desired reaction.

The test element 18 is adapted to be placed into contact with the fluid sample (e.g., a whole blood sample) to be tested. The whole blood sample may be generated by a lancing device such as a lancet. The whole blood sample may be obtained by a lancet that may be separate from the meter or may be integrated within the meter. The lancing device may obtain blood by, for example, pricking a person's finger.

Figure 2:
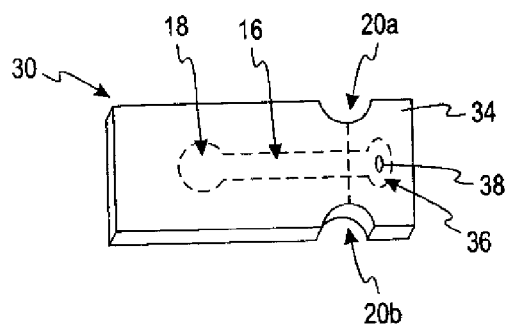
FIG. 2 is an upper perspective view of the test strip of FIG. 1a having a desiccated cavity, according to another embodiment of the present invention.

Referring now to FIG. 2, a test strip 30 is illustrated according to one embodiment of the present invention. The test strip 30 includes a cavity 36 within the tab 34 of the test strip 30. The cavity 36 is connected to the capillary channel 16, and thus, is in communication with the test element 18. The cavity 36 may contain a desiccant 38 for removing moisture from the test element 18, capillary channel 16, and cavity 36. The desiccant 38 may be, for example, a desiccant bead or hot melt desiccant plug, located in the cavity 36. In other embodiments, the cavity 36 and the desiccant 38 are located within the base 12 of the test strip 10 yet remain in gaseous communication with both the test element 18 and the capillary channel 16. After the tab 34 has been removed, the test strip 30 is identical to the test strip 10 shown in FIG. 1b.

In the embodiments of FIGS. 1-2, the test strips are self-contained ampoules. An ampoule is a small container that is sealed to the external elements. As discussed with respect to FIG. 2, a desiccant may be provided in the ampoule. Thus, the test strips of the present invention do not require an instrument designer to devise a reliable, resealable inner cartridge to hold the test strips. The test strips may be laminated or may be molded and formed to the designs illustrated above. The base 12 of the test strips may be made of any suitable material, as is generally known within the art. For example, where the reaction between the reactants and the fluid sample is to be monitored optically, the base 12 of the test strip may be designed from an optically clear material, such as, optically clear polyethylene terephthalate (PET).

The tab 14 of the test strips may be a stiff plastic, or alternatively, a flexible material that can be punctured or torn to reveal the inlet 24 to the capillary channel 16.

Figure 3:
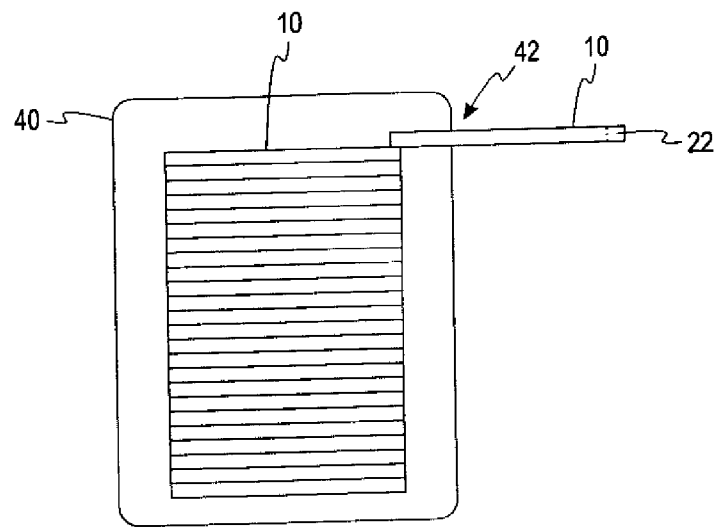
FIG. 3 is a cross-sectional view of a cartridge adapted to contain a plurality of test strips, according to one embodiment of the present invention.

Turning now to FIG. 3, a cartridge 40 adapted to store and eject a plurality of test strips 10 is illustrated, according to one embodiment. The cartridge 40 includes an opening 42 adapted to allow a test strip 10 to be ejected therefrom. The cartridge 40 includes an ejection mechanism (not shown) for allowing a user to eject a test strip 10 from the cartridge 40. The ejection mechanism is adapted to eject a test strip 10 such that at least the tab 14 and the break line 22 are external from the cartridge 40 after the test strip 10 has been ejected.

Once the test strip 10 has been ejected, a user may expose the inlet 24 by tearing, puncturing, ripping, or otherwise separating the tab 14 from the base 12. Alternatively, the tab 14 may be separated from the base 12 during the ejection of the test strip 10 from the cartridge 40. Once the tab 14 has been separated, a user may bring the inlet 24 of the base 12 into contact with a fluid sample. The fluid sample is then transported to the test element 18 and the test strip 10 may be repositioned—either manually or by the cartridge 40 or meter—so that the meter is able to determine the analyte concentration in the fluid sample.

Figure 4A:
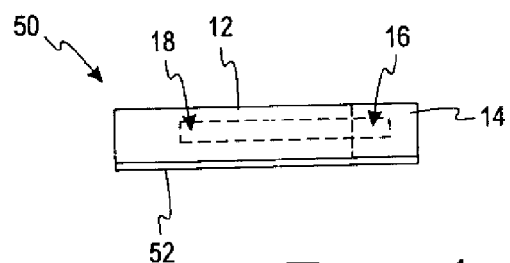
FIG. 4a is a side view of a test strip having a removably attached flexible strip, according to yet another embodiment of the present invention.
Figure 4B:
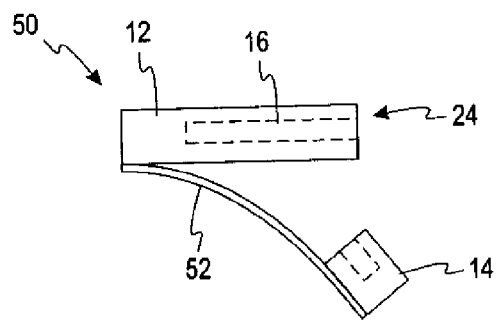
FIG. 4b is a side view of the test strip of FIG. 4a having the flexible strip partially separated from the base.

Turning now to FIGS. 4a-b, a test strip 50 is illustrated having a flexible strip 52 attached thereto. The flexible strip 52 is removably attached to the base 12 and is attached to the tab 14 of the test strip 50. As illustrated in FIGS. 4a-b, when the tab 14 is separated from the base 12 to expose the inlet 24, the flexible strip 52 allows the tab 14 and base 12 to remain an unified piece. Thus, the tab 14 would be discarded along with the base 12 when the test strip 50 is no longer required. Alternatively, in other embodiments, the flexible strip 52 is completely separated from the base 12 while remaining attached to the tab 14.

Figure 5A:
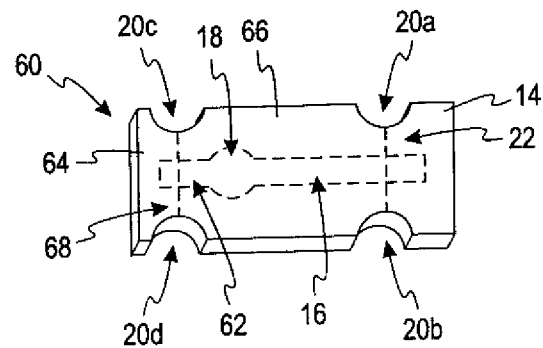
FIG. 5a is an upper perspective view of a test strip, according to one embodiment of the present invention.
Figure 5B:
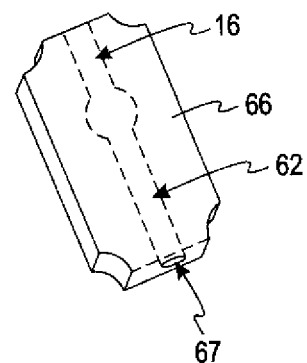
FIG. 5b is an upper perspective view of the test strip of FIG. 5a after the tabs have been separated from the base.

Turning now to FIGS. 5a-b, a test strip 60 is illustrated according to one embodiment of the present invention. The test strip 60 includes a vent channel 62 that is in gaseous communication with the test element 18 and the capillary strip 16. The vent channel 62, when exposed, allows air to escape from the capillary channel 16 and test element 18 as a fluid sample enters. The test strip 60 includes a second tab 64 and a second set of recesses 20c,d that facilitate the separation of the second tab 64 from a base 66 along a second break line 68. The separation of the second tab 64 from the base 66 exposes a vent 67 at the end of the base 66 along the break line 68. In this embodiment, a user or the device separates both the first tab 14 and the second tab 64 from the base 66 to expose an inlet 24 (FIG. 1b) and the vent 67. As a fluid sample enters the inlet 24, the displaced gas from the capillary channel 16 and the test element 18 are allowed to escape through the vent channel 62 and out the vent 67.

Figure 6A:
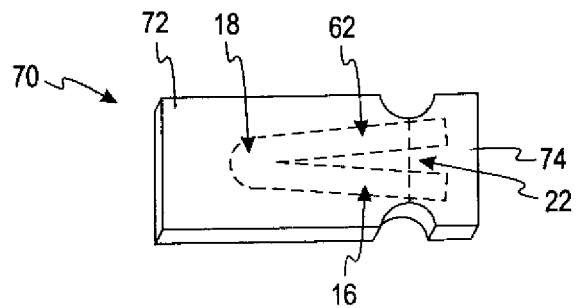
FIG. 6a is an upper perspective view of a test strip, according to another embodiment of the present invention.
Figure 6B:
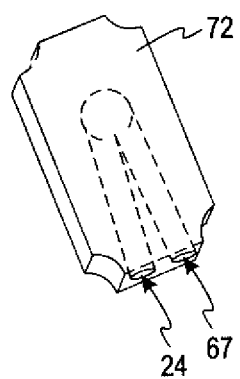
FIG. 6b is an upper perspective view of the test strip of FIG. 6a after the tab has been separated from the base.

Referring now to FIGS. 6a-b, a venting channel 62 is illustrated within a test strip 70, according to another embodiment of the present invention. The test strip 70 is designed to allow a single separation of a tab 74 from a base 72 to expose both an inlet 24 and a vent 67. As illustrated in FIG. 6a, the break line 22 intersects both the capillary channel 16 and the vent channel 62.

Figure 7A:
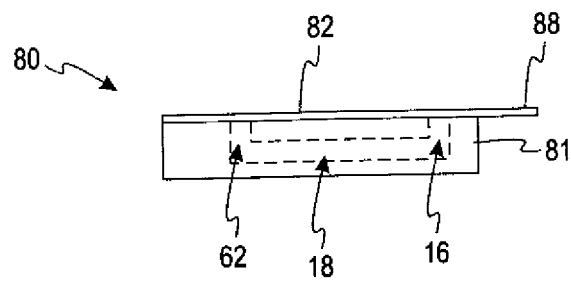
FIG. 7a is a side view of a test strip having a foil tab, according to yet another embodiment of the present invention.
Figure 7B:
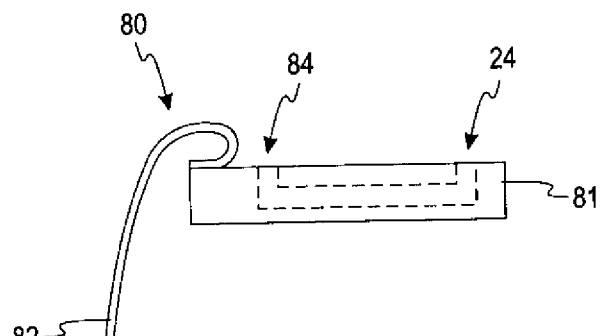
FIG. 7b is a side view of the test strip of FIG. 7a with the foil tab partially separated from the base.
Figure 7C:
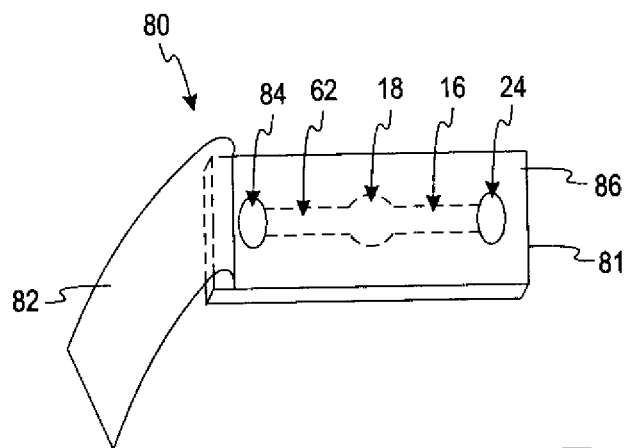
FIG. 7c is an upper perspective view of the test strip of FIG. 7a with the foil tab partially separated from the base.

Turning now to FIGS. 7a-c, a test strip 80 is illustrated according to one embodiment of the present invention. A base 81 of the test strip 80 includes a capillary channel 16, a test element 18, and a vent channel 62, as shown in FIG. 1a. A tab 82 of the test strip 80 is removably attached to an upper surface 86 of the base 81. The tab 82 includes a lip or extension 88 that extends from the tab 82 past the base 81. The lip 88 is adapted to allow a user or device to remove the tab 82 from the base 81. For example, a user may grasp the lip 88 and peel the tab 82 from the base 81. When the tab 82 has been sufficiently removed from the base 81, an inlet 24 and a vent 84 are exposed, as is best illustrated in FIG. 7b-c.

The tab 82 may be designed from any suitable material. For example, the tab 82 may be made of standard foil. The tab 82 may be attached to the base 81, for example, by an adhesive (e.g., pressure-sensitive adhesive, hot-mount adhesive, etc.) The tab 82 may be designed so as to remove entirely from the base 81 or may remain partially attached to the base 81, as shown in FIGS. 7b-c.

Figure 8A:
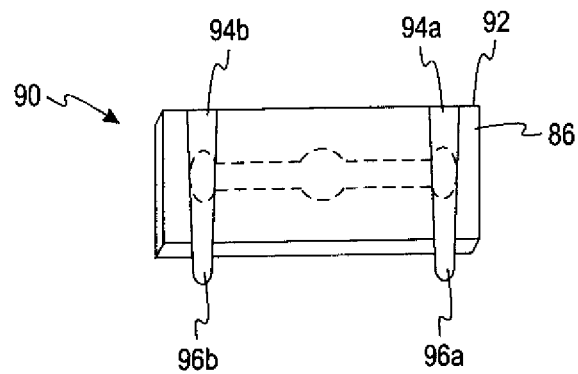
FIG. 8a is an upper view of a test strip having a plurality of tab strips, according to one embodiment of the present invention.
Figure 8B:
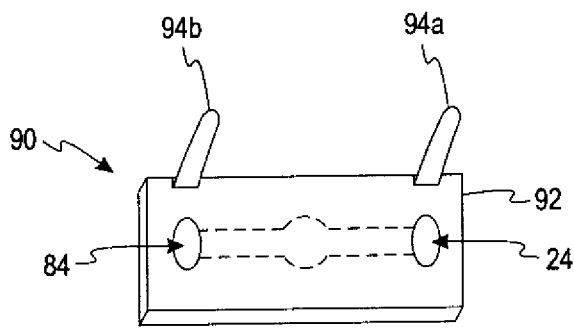
FIG. 8b is an upper view of the test strip of FIG. 8a having a plurality of tab strips partially separated from the base.

Turning now to FIGS. 8a-b, a test strip 90 is illustrated according to one embodiment of the present invention. The test strip 90 includes a first tab strip 94a and a second tab strip 94b. The tab strips 94a,b cover an inlet 24 and a vent 84 respectively. The tab strips 94a,b are removably attached to an upper surface 86 of the base 82 of the test strip 90. Each tab strip 94a,b includes a lip or extension 96a,b respectively that extends beyond the base 82, as illustrated in FIG. 8a. The tab strips 94a,b may be peeled from the base 82, for example, by grasping the extensions 96a,b and pulling the tab strips 94a,b back across the base 82, opposite the original position of the extensions 96a,b in FIG. 8a.

The tab strips 94a,b may be designed from any suitable material, such as the materials described above with respect to tab 82 in FIGS. 7a-c. Additionally, a string or an oriented polymer may be embedded in the tab strips 94a,b to provide support when peeling the tab strips 94a,b. The tab strips 94a,b may be designed so as to remove entirely from the base 82 or may remain attached to the base 82 as shown in FIG. 8b.

Figure 9:
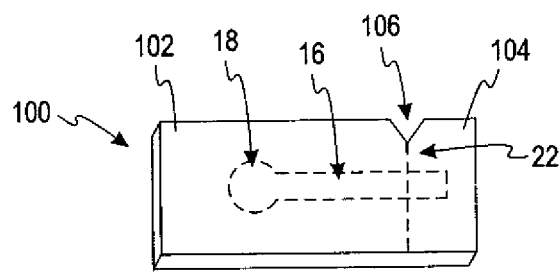
FIG. 9 is an upper view of a test strip, according to another embodiment of the present invention.

Turning now to FIG. 9, a test strip 100 is illustrated according to another embodiment of the present invention. The test strip 100 includes a notch 106 located between a base 102 and a tab 104. The notch 106 is adapted to allow the tab 104 to be torn from the base 102 along the break line 22. After the tab 104 has been removed, the test strip 100 is similar to the test strip 10 shown in FIG. 1b.

Figure 10A:
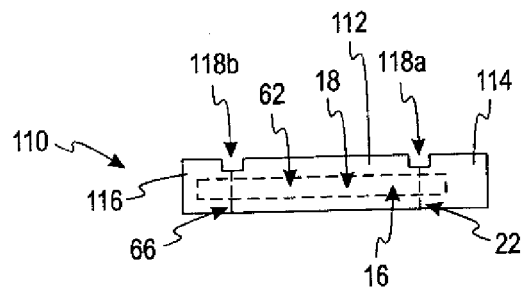
FIG. 10a is a side view of a test strip having a plurality of depressions, according to yet another embodiment of the present invention.

Turning now to FIG. 10a, a test strip 110 is illustrated according to one embodiment of the present invention. The test strip 110 includes a base 112 located between a first tab 114 and a second tab 116. A first depression 118a is between the first tab 114 and the base 112 and a second depression 118b is located between the second tab 116 and the base 112. The depressions 118a,b are adapted to allow an inlet (not shown) and a vent (not shown) to be exposed along the respective break lines 22, 66.

Figure 10B:
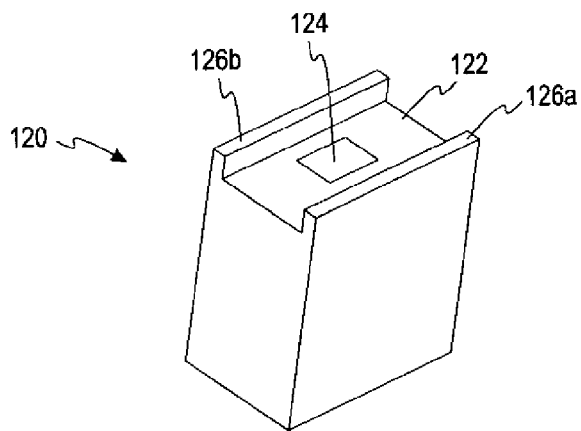

Referring now to FIG. 10b, a meter 120 is illustrated according to one embodiment of the present invention. The meter 120 is adapted to seat the test strip 110 of FIG. 10a. The meter 120 may be a generally rectangular box (though other designs are known and may be adapted for use with the present invention). The meter 120 includes a face 122 having a read-head 124 located therein. The read-head 124 may be used to analyze a fluid sample located on the test strip 110. The meter 120 includes a plurality of projections 126a,b that are adapted to engage the base 112 of the test strip 110. The projections 126a,b are designed to position the test element 18 of the test strip 110 proximate the read-head 124 of the meter 120.

Figure 10C:
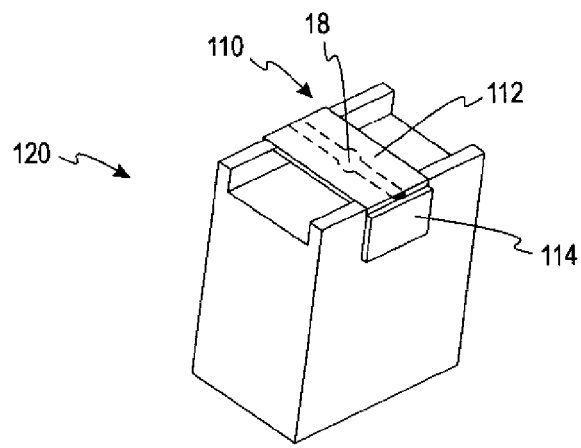
FIG. 10c is an upper perspective view of the meter of FIG. 10b having the test strip of FIG. 10a seated thereon.

Once the test strip 110 has been seated on the meter 120, the first and second tabs 114,116 may be separated from the base 112 along the break lines 22,66, as illustrated in FIG. 10c. The meter 120 facilitates separation of the tabs 114,116 from the base 112 by holding the base 112 in position as a pressure is applied to the tabs 114,116 in the direction of the meter 120. The tabs 114,116 may be completely separated from the base 112, or the tabs 114,116 may remain attached to the base 112 as illustrated in FIG. 10c. The bending of the tabs 114,116 may be effected either manually or mechanically. Mechanical bending of the tabs 114,116 can be effected by a moving piece within the meter 120, or movement of the test strip 110 within the meter 120 against stationary projections which perform the bending of the tabs 114,116.

Figure 11A:
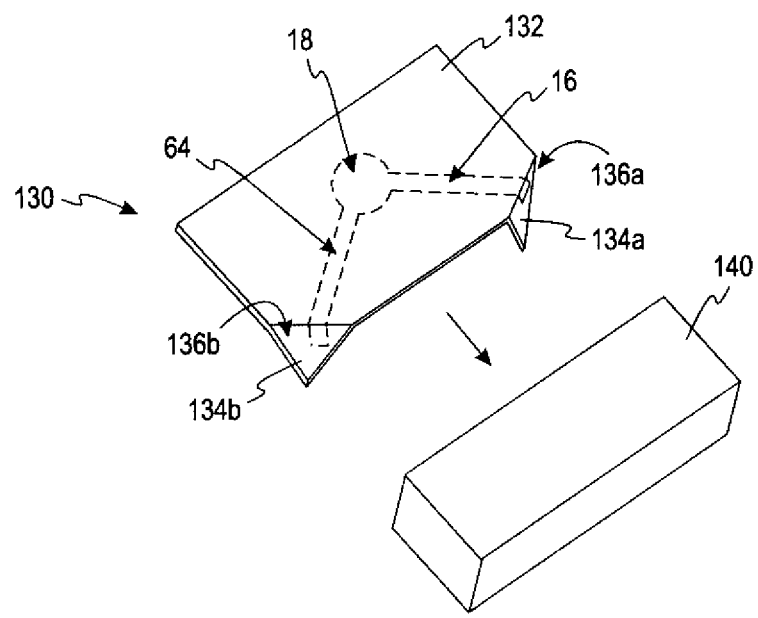
FIG. 11a is an upper perspective view of a test strip and opening device, according to one embodiment of the present invention.
Figure 11B:
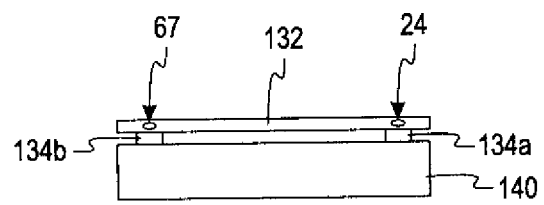
FIG. 11b is a side view of the test strip of FIG. 11a once the tabs have been partially separated from the base by the opening device.

Referring now to FIGS. 11a-b, a test strip 130 and opening device 140 are illustrated according to one embodiment of the present invention. The opening device 140 may be incorporated into a meter that can be used to read the test element and determine the concentration of one or more analyte in a fluid sample. The test strip 130 includes one or more tabs 134. In the illustrated embodiment, the test strip 130 includes two tabs 134a,b. The tabs 134 are located perpendicular to the base 132 and may be triangular (as shown) or any other suitable shape. As the test strip 130 is moved past the opening device 140, for example, as the test strip is being moved to a ready position or ejected from a cartridge, the tabs 134 are brought into contact with the opening device 140 and are bent toward the base 132, thus, exposing an inlet 24 and/or vent 67 along the break lines 134a,b, as illustrated in FIG. 11b.

As discussed above, an instrument or meter can perform the automatic opening of the test strip as the test strip is moved to a ready area for inoculation by a fluid sample. For example, according to some embodiments, a foil tab located above the base with a slight gap allows the instrument or meter to passively open the sensor with a knife or blade as the test strip is moved into the ready area. Alternatively, in some embodiments where a gear is used to move the test strip to the ready area, a sprocket could expose a vent and inlet by poking through the tab as the test strip is being positioned.

Figure 12A:
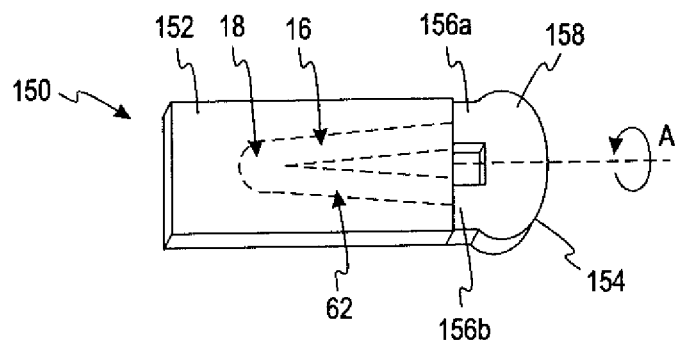
FIG. 12a is an upper perspective view of a test strip, according to one embodiment of the present invention.
Figure 12B:
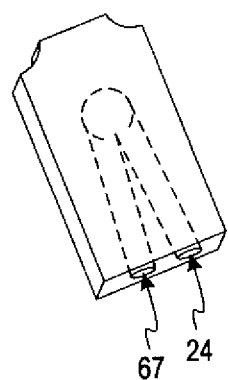
FIG. 12b is an upper perspective view of the test strip of FIG. 12a after the tab has been separated from the base.

Turning now to FIGS. 12a-b, a test strip 150 is illustrated according to another embodiment of the present invention. The test strip 150 is a twist-off test strip having a base 152 removably attached to a tab 154. The tab 154 includes one or more extensions 156. In the illustrated embodiment, the tab 154 includes two extensions 156a,b that extend from a body 158 of the tab 154. The extensions 156a,b are removably attached to the base 152, thus, attaching the base 152 to the tab 154. The extensions 156a,b are attached to the base 152 at an inlet 24 and/or at a vent 67 to seal one or more of the capillary channel 16 or the vent channel 62.

To expose the inlet and/or vent, a user or instrument may rotate the tab 154 around an axis running (in the embodiment illustrated in FIG. 12a) between, and parallel to, the extensions 156a,b. For example, by rotating the tab 154 in the direction of arrow A. Alternatively, the tab 154 may be rotated opposite arrow A. The tab 154 and/or base 152 may be designed from a soft-plastic to facilitate the removal of the tab 154 from the base 152 when the tab 154 is rotated.

Figure 13A:
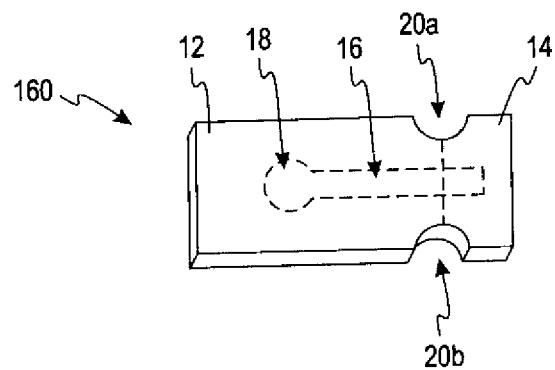
FIG. 13a is an upper perspective view of a test strip, according to one embodiment of the present invention.
Figure 13B:
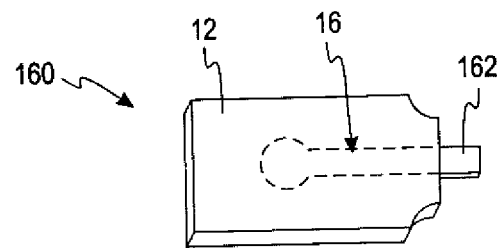
FIG. 13b is an upper perspective view of the test strip of FIG. 13a once the tab has been removed, according to one embodiment of the present invention.

Referring now to FIGS. 13a-b, a test strip 160 is illustrated according to one embodiment of the present invention. The test strip 160 is similar to the test strip 10 described in FIGS. 1a-b. However, in some embodiments, like the embodiment illustrated in FIGS. 13a-b, the test strip 160 includes protrusion 162 that extends from the base 12 and extends the capillary channel 16 such that an inlet 164 is removed from the base 12. In these embodiments, the protrusion 162 helps to prevent or inhibit contamination of a meter or read-head by a sample when the sample is being applied with the test strip 160 positioned on the meter.

In some embodiments of the present invention, the above-described protrusion 162 is incorporated into each of the above-described test strips. In some embodiments where the test strip includes a vent channel, it is desirable to prevent a fluid sample from entering the vent channel. If the fluid sample is allowed to enter the vent channel, a larger fluid sample is required. However, when the fluid sample is being obtained directly from a user (e.g., a blood sample from the user's fingertip) it may be desirable to reduce the volume of the required fluid. Thus, in embodiments having a vent channel, it may be desirable to prevent or inhibit the fluid sample from entering the vent channel.

Additionally, in some embodiments the capillary channel is treated to assist in transporting the fluid sample to the test element. For example, the capillary channel may be treated with a hydrophilic coating, a hydrophilic mesh, or a hydrophilic graft polymer. In embodiments where the fluid sample is blood, the capillary channel may be treated with plasma or corona discharge to induce the blood drop to enter.

One method to assist in preventing or inhibiting the fluid sample from entering the vent channel is to treat only the capillary channel as discussed above, while not treating the vent channel. Alternatively or additionally, the vent channel could be blocked by a hydrophobic air permeable material (e.g., mesh, scintered plastic bead membrane such as Porex, scintered metal or metal sponge, hydrophobic venting membranes such as teflon or polyolefins, etc.), a hydrophobic stripe (e.g., hot melt or laminated hydrophobic plastic), a chemical treatment to render hydrophobicity, or by removing any pretreatment by physical means (e.g., laser ablation, localized heating, or mechanical scoring).

Another method to assist in preventing the fluid sample from entering the vent channel is to vary the depth of the vent channel in comparison to the test element. For example, the vent channel could be deeper than the test element and the resulting height differential would prevent or inhibit fluid sample flow into the vent channel.

According to some embodiments of the present invention, the integrity of each strip can be automatically tested by a meter. For example, in some embodiments, a colorimetric indicator that would indicate the presence of an undesirable substance (e.g., water, etc.) can be used to determine the strip integrity. The indicator could be read by a read-head within the meter—the same read-head used to read the test element once the fluid sample has been applied. In this way, an objective determination as to the integrity of the test strip can be made. In other embodiments, automated electrochemical determinations of desiccant saturation can be made. For example, in electrochemical systems, desiccant moisture content (indicating strip integrity) may be determined by electrochemical means (e.g., conductance, resistance, impedance, capacitance, etc.) sensitive to water content.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

Alternative Embodiment A

A test strip to assist in determining the concentration of an analyte in a fluid sample, comprising:

a base including a capillary channel and a test element, the capillary channel being in fluid communication with the test element, the test element being adapted to receive the fluid sample;

at least one tab removably attached to the base, the capillary channel extending from the base into a portion of the tab; and a break line intersecting the capillary channel, wherein an inlet to the capillary channel is exposed along the break line when the tab is separated from the base.

Alternative Embodiment B

The test strip of Alternative Embodiment A further comprising at least one recess located between the base and the at least one tab, the at least one recess being adapted to facilitate the separation of the at least one tab from the base along the break line.

Alternative Embodiment C

The test strip of Alternative Embodiment B further comprising a second recess located between the base and the at least one tab opposite the at least one recess, the at least one recess and second recess facilitating the separation of the at least one tab from the base along the break line.

Alternative Embodiment D

The test strip of Alternative Embodiment A wherein the at least one tab includes a cavity having a desiccant located therein, the cavity being in gaseous communication with the capillary channel and the test element.

Alternative Embodiment E

The test strip of Alternative Embodiment A wherein the base includes a vent channel, the vent channel being in communication with the test element and the capillary channel.

Alternative Embodiment F

The test strip of Alternative Embodiment E wherein the at least one tab includes a cavity having a desiccant located therein, the cavity being in gaseous communication with the capillary channel, the test element, and the vent channel.

Alternative Embodiment G

The test strip of Alternative Embodiment E wherein the at least one tab includes a cavity having a desiccant located therein, the cavity being in liquid communication with the capillary channel, the test element, and the vent channel.

Alternative Embodiment H

The test strip of Alternative Embodiment E wherein the vent channel includes a desiccant located therein.

Alternative Embodiment I

The test strip of Alternative Embodiment E wherein the break line intersects the vent channel.

Alternative Embodiment J

The test strip of Alternative Embodiment I wherein a vent to the vent channel is exposed along the break line when the at least one tab is separated from the base.

Alternative Embodiment K

The test strip of Alternative Embodiment E further comprising a second tab removably attached to the base opposite the at least one tab, the vent channel extending from the base into the second tab.

Alternative Embodiment L

The test strip of Alternative Embodiment K wherein a vent is exposed when the second tab is separated from the base.

Alternative Embodiment M

The test strip of Alternative Embodiment A further comprising a flexible strip removably attached to the base, the flexible strip at least partially separating from the base when the at least one tab is separated from the base, the flexible strip remaining attached to the at least one tab.

Alternative Embodiment N

The test strip of Alternative Embodiment A further comprising a notch adapted to facilitate the tearing of the at least one tab from the base along the break line.

Alternative Embodiment O

The test strip of Alternative Embodiment A wherein the break line is formed by scoring the test strip.

Alternative Embodiment P

The test strip of Alternative Embodiment A wherein the break line is formed by a cut line in the test strip.

Alternative Embodiment Q

The test strip of Alternative Embodiment A wherein the break line is formed by a line of weakness along the test strip.

Alternative Embodiment R

The test strip of Alternative Embodiment A wherein the break line is formed by a thinned area of the test strip.

Alternative Embodiment S

The test strip of Alternative Embodiment A wherein the test element contains a desiccant in gaseous communication with the test element.

Alternative Embodiment T

The test strip of Alternative Embodiment A wherein the test element contains a desiccant in liquid communication with the test element.

Alternative Process U

A method for using a test strip to determine a concentration of an analyte in a fluid sample, the method comprising the acts of:
 providing a test strip including
  (i) a base including a capillary channel and a test element, the capillary channel being in fluid communication with the test element, the test element being adapted to receive the fluid sample,
  (ii) at least one tab removably attached to the base, the capillary channel extending from the base into a portion of the tab, and
  (iii) a break line intersecting the capillary channel;
 exposing an inlet to the capillary channel by at least partially separating the at least one tab from the base.

Alternative Process V

The method of Alternative Process U wherein an opening device is used to expose the inlet.

Alternative Process W

The method of Alternative Process U wherein the at least one tab is at least partially separated from the base by a meter.

Alternative Process X

The method of Alternative Process U wherein the at least one tab is at least partially separated from the base by twisting the at least one tab relative to the base.

Alternative Process Y

The method of Alternative Process U wherein the at least one tab is at least partially separated from the base by tearing the test strip along the break line.

Alternative Process Z

The method of Alternative Process U wherein the at least one tab is at least partially separated from the base by bending the test strip at the break line.

Alternative Process AA

The method of Alternative Process U wherein the at least one tab is at least partially separated from the base by slicing the test strip at the break line.

Alternative Process AB

The method of Alternative Process U wherein the at least one tab is at least partially separated from the base by pulling the at least one tab away from the base.

Alternative Embodiment AC

A test strip to assist in determining the concentration of an analyte in a fluid sample, comprising:

a base including a capillary channel and a test element, the capillary channel being in fluid communication with the test element, the test element being adapted to receive the fluid sample;

a tab removably attached to the base, the capillary channel extending from the base into a portion of the tab;

a protrusion extending from the base into the tab, the protrusion being an extension of the capillary channel into the tab; and a break line intersecting the capillary channel, wherein an inlet to the capillary channel is exposed when the tab is separated from the base, the inlet being located at the end of the protrusion opposite the base.

Alternative Embodiment AD

The test strip of Alternative Embodiment AC further comprising at least one recess located between the base and the tab, the at least one recess being adapted to facilitate the separation of the tab from the base along the break line.

Alternative Embodiment AE

The test strip of Alternative Embodiment AC wherein the tab includes a cavity having a desiccant located therein, the cavity being in gaseous communication with the capillary channel and the test element.

Alternative Embodiment AF

The test strip of Alternative Embodiment AC wherein the tab includes a cavity having a desiccant located therein, the cavity being in liquid communication with the capillary channel and the test element.

Alternative Embodiment AG

The test strip of Alternative Embodiment AC wherein the base includes a vent channel, the vent channel being in communication with the test element and the capillary channel.

Alternative Embodiment AH

The test strip of Alternative Embodiment AG wherein the tab includes a cavity having a desiccant located therein, the cavity being in gaseous communication with the capillary channel, the test element, and the vent channel.

Alternative Embodiment AI

The test strip of Alternative Embodiment AG wherein the vent channel includes a desiccant located therein.

Alternative Embodiment AJ

The test strip of Alternative Embodiment AG wherein the break line intersects the vent channel.

Alternative Embodiment AK

The test strip of Alternative Embodiment AJ wherein a vent to the vent channel is exposed when the tab is separated from the base.

Alternative Embodiment AL

The test strip of Alternative Embodiment AC further comprising a notch adapted to facilitate the tearing of the tab from the base along the break line.

Alternative Embodiment AM

A test strip to assist in determining the concentration of an analyte in a fluid sample, comprising:

a base including an upper surface, a capillary channel, a test element, and a desiccant, the capillary channel being in fluid communication with the test element, the test element being adapted to receive the fluid sample; and at least one tab removably attached to the upper surface of the base, the at least one tab including a lip that extends from the base, the lip being adapted to allow the at least one tab to be separated such that the separation from the base exposes an inlet to the capillary channel.

Alternative Embodiment AN

The test strip of Alternative Embodiment AM wherein the base includes a cavity, the desiccant being located within the cavity, the cavity being in gaseous communication with the capillary channel and the test element.

Alternative Embodiment AO

The test strip of Alternative Embodiment AM wherein the base includes a vent channel, the vent channel being in communication with the test element and the capillary channel.

Alternative Embodiment AP

The test strip of Alternative Embodiment AO wherein the base includes a cavity, the desiccant being located within the cavity, the cavity being in gaseous communication with the capillary channel, the test element, and the vent channel.

Alternative Embodiment AQ

The test strip of Alternative Embodiment AO wherein the base includes a cavity, the desiccant being located within the cavity, the cavity being in liquid communication with the capillary channel, the test element, and the vent channel.

Alternative Embodiment AR

The test strip of Alternative Embodiment AO wherein the desiccant is located within the vent channel.

Alternative Embodiment AS

The test strip of Alternative Embodiment AO wherein the separation of the at least one tab from the base exposes a vent to the vent channel.

Alternative Embodiment AT

The test strip of Alternative Embodiment AM further comprising a second tab, the second tab including a second lip that extends from the base, the second lip being adapted to allow the second tab to be separated from the base.

Alternative Embodiment AU

The test strip of Alternative Embodiment AO wherein the separation of the at least one tab from the base exposes an inlet to the capillary channel while the separation of the second tab from the base exposes a vent of the vent channel.

Alternative Embodiment AV

A test strip to assist in determining the concentration of an analyte in a fluid sample, comprising:
a base including a capillary channel, a test element, and a vent channel, the test element being adapted to receive the fluid sample, the capillary channel, test element, and vent channel being in communication with one another;
a first tab removably attached to the base, the capillary channel extending from the base into a portion of the first tab;
a second tab removably attached to the base, the second tab being located opposite the base from the first tab, the vent channel extending from the base into a portion of the second tab;
a first break line intersecting the capillary channel, wherein an inlet to the capillary channel is exposed when the first tab is separated from the base; and
a second break line intersecting the vent channel, wherein a vent to the vent channel is exposed when the second tab is separated from the base.

Alternative Embodiment AW

The test strip of Alternative Embodiment AV further comprising a first depression located between the base and the first tab, the first depression facilitating the separation of the first tab from the base along the first break line.

Alternative Embodiment AX

The test strip of Alternative Embodiment AW further comprising a second depression located between the base and the second tab, the second depression facilitating the separation of the second tab from the base along the second break line.

Alternative Embodiment AY

A test strip to assist in determining the concentration of an analyte in a fluid sample, comprising:
a base including a capillary channel and a test element, the capillary channel being in fluid communication with the test element, the test element being adapted to receive the fluid sample; and
a tab having a body and at least one extension extending from the body of the tab, the at least one extension removably attaching the base to the tab,
wherein the at least one extension is adapted to separate from the base when the tab is rotated relative to the base.

Alternative Embodiment AZ

The test strip of Alternative Embodiment AY wherein the base includes a cavity having a desiccant located therein, the cavity being in gaseous communication with the capillary channel and the test element.

Alternative Embodiment BA

The test strip of Alternative Embodiment AY wherein the base includes a vent channel, the vent channel being in communication with the test element and the capillary channel.

Alternative Embodiment BB

The test strip of Alternative Embodiment BA wherein the base includes a cavity having a desiccant located therein, the cavity being in gaseous communication with the capillary channel, the test element, and the vent channel.

Alternative Embodiment BC

The test strip of Alternative Embodiment BA wherein the vent channel includes a desiccant located therein.

Alternative Embodiment BD

The test strip of Alternative Embodiment AY wherein an inlet to the capillary channel is exposed when the at least one extension is separated from the base.

Alternative Embodiment BE

The test strip of Alternative Embodiment BA wherein a vent to the vent channel is exposed when the at least one extension is separated from the base.

Alternative Embodiment BF

A test strip to assist in determining the concentration of an analyte in a fluid sample, comprising:
a base including a capillary channel and a test element, the capillary channel being in fluid communication with the test element, the test element being adapted to receive the fluid sample; and
at least one tab removably attached to the base, the at least one tab being located perpendicular to the base, the at least one tab being adapted to bend toward the base to expose an inlet to the capillary channel.

Alternative Embodiment BG

The test strip of Alternative Embodiment BF wherein the base includes a vent channel, the vent channel being in communication with the test element and the capillary channel.

Alternative Embodiment BH

The test strip of Alternative Embodiment BG wherein the at least one tab is bent toward the base by an opening device.

Alternative Embodiment BI

The test strip of Alternative Embodiment BG wherein the opening device is incorporated into a meter adapted to read the test element and determine the analyte concentration in the fluid sample.

Alternative Embodiment BJ

The test strip of Alternative Embodiment BG wherein the at least one tab is bent toward the base as the test strip is being move to a ready position.

Alternative Embodiment BK

The test strip of Alternative Embodiment BG wherein the at least one tab is bent toward the base as the test strip is being ejected from a cartridge.

Alternative Embodiment BL

The test strip of Alternative Embodiment BF wherein the at least one tab is substantially triangular.

Alternative Embodiment BM

A meter adapted to incorporate a test strip to assist in determining the concentration of an analyte in a fluid sample, the meter comprising:
a face having a read-head located therein; and
a plurality of projections extending from the face, the plurality of projections being adapted to seat the test strip thereon, the test strip including
(i) a base including a capillary channel and a test element, the capillary channel being in fluid communication with the test element, the test element being adapted to receive the fluid sample,
(ii) at least one tab removably attached to the base, the capillary channel extending from the base into a portion of the tab; and
(iii) a break line intersecting the capillary channel, wherein an inlet to the capillary channel is exposed along the break line when the tab is separated from the base.

Alternative Embodiment BN

The meter of Alternative Embodiment BM wherein the meter facilitates the separation of the at least one tab from the base of the test strip.

Alternative Embodiment BO

The meter of Alternative Embodiment BM wherein the test element of the test strip is proximate the read-head of the meter when the test strip is seated on the meter.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents and alternatives falling within the spirit and scope of the invention as defined by the appended claims.

The invention claimed is:
1. A test strip cartridge, comprising:
a housing including an opening;
an ejection mechanism configured to eject a test strip from the housing and through the opening; and
a plurality of test strips positioned within the housing, each of the plurality of test strips having:
a base including a capillary channel having at least one interior surface with a reagent deposited thereon;
a tab removably attached to an end of the base, the capillary channel extending from the base into a portion of the tab such that the tab includes a portion of the capillary channel; and
a break line intersecting the capillary channel, wherein an inlet to the capillary channel is configured to be exposed along the break line in response to the tab being at least partially separated from the base.

2. The test strip cartridge of claim 1, wherein each of the plurality of test strips further has at least one recess located between the base and the tab, the at least one recess being adapted to facilitate the separation of the tab from the base along the break line.

3. The test strip cartridge of claim 1, wherein the tab of each of the plurality of test strips includes a cavity having a desiccant located therein, the cavity being in communication with the capillary channel and the reagent.

4. The test strip cartridge of claim 1, wherein the base of each of the plurality of test strips includes a vent channel in communication with the capillary channel.

5. The test strip cartridge of claim 4, wherein the break line of each of the plurality of test strips intersects the vent channel.

6. The test strip cartridge of claim 5, wherein a vent to the vent channel of each of the plurality of test strips is configured to be exposed along the break line in response to the tab being at least partially separated from the base.

7. The test strip cartridge of claim 4, wherein each of the plurality of test strips further comprises a second tab removably attached to a second end of the base opposite the first end of the base, the vent channel extending from the base into the second tab such that the second tab includes a portion of the vent channel.

8. The test strip cartridge of claim 7, wherein a vent to the vent channel of each of the plurality of test strips is configured to be exposed in response to the second tab being at least partially separated from the base.

9. The test strip cartridge of claim 1, wherein the break line of each of the plurality of test strips is formed by a line of weakness along the test strip.

10. The test strip cartridge of claim 1, wherein the break line of each of the plurality of test strips is formed by scoring the test strip.

11. The test strip cartridge of claim 1, wherein the break line of each of the plurality of test strips is formed by a cut line in the test strip.

12. The test strip cartridge of claim 1, wherein the break line of each of the plurality of test strips is formed by a thinned area of the test strip.

13. The test strip cartridge of claim 1, wherein the ejection mechanism is configured to eject the test strip such that at least the tab and the break line of the test strip are external from the housing after the test strip is ejected.

14. A method of using a test strip cartridge, comprising:
ejecting one of a plurality of test strips from a test strip cartridge through an opening of a housing of the test strip cartridge using an ejection mechanism of the test strip cartridge, the ejected test strip comprising (i) a base including a capillary channel having at least one interior surface with a reagent deposited thereon, (ii) a tab removably attached to an end of the base, the capillary channel extending from the base into a portion of the tab such that the tab includes a portion of the capillary channel, and (iii) a break line intersecting the capillary channel; and
exposing an inlet to the capillary channel along the break line by at least partially separating the tab from the base.

15. The method of claim 14, further comprising receiving a fluid sample through the inlet such that the fluid sample flows through the capillary channel and contacts the reagent.

16. The method of claim 14, wherein the tab is at least partially separated from the base by moving the base within a meter having projections positioned to apply pressure to the tab.

17. The method of claim 14, wherein the tab is at least partially separated from the base by twisting the tab relative to the base.

18. The method of claim 14, wherein the tab is at least partially separated from the base by tearing the test strip along the break line.

19. The method of claim 14, wherein the tab is at least partially separated from the base by bending the test strip at the break line.

20. The method of claim 14, wherein the tab is at least partially separated from the base by slicing the test strip at the break line.

21. The method of claim 14, wherein the tab is at least partially separated from the base by pulling the first tab away from the base.

22. The method of claim 14, wherein the ejecting comprises ejecting the one of the plurality of test strips such that at least the tab and the break line of the one of the plurality of test strips are external from the housing.

* * * * *